United States Patent [19]
Eichman

[11] Patent Number: 5,980,882
[45] Date of Patent: Nov. 9, 1999

[54] DRUG-RESIN COMPLEXES STABILIZED BY CHELATING AGENTS

[75] Inventor: Martin L. Eichman, Fairport, N.Y.

[73] Assignee: Medeva Pharmaceuticals Manufacturing, Rochester, N.Y.

[21] Appl. No.: 08/834,359

[22] Filed: Apr. 16, 1997

[51] Int. Cl.⁶ .............................. A61K 47/32; A61K 9/30
[52] U.S. Cl. ...................... 424/78.12; 424/78.1; 424/483
[58] Field of Search ................................ 424/78.1, 78.11, 424/78.12, 78.13, 78.14, 78.15, 78.16, 78.17, 483

[56] References Cited

U.S. PATENT DOCUMENTS

| | | |
|---|---|---|
| 2,697,059 | 12/1954 | Gustus . |
| 2,751,325 | 6/1956 | Wendt . |
| 2,990,332 | 6/1961 | Keating ................................ 424/48.1 |
| 3,035,984 | 5/1962 | Mierswa . |
| 3,070,503 | 12/1962 | Siegel et al. . |
| 3,070,508 | 12/1962 | Siegel et al. . |
| 3,100,738 | 8/1963 | Cavallito . |
| 3,108,044 | 10/1963 | Rety et al. . |
| 3,143,465 | 8/1964 | Keating ................................ 424/78.1 |
| 3,352,801 | 11/1967 | White . |
| 3,499,960 | 3/1970 | Macek et al. . |
| 3,594,470 | 7/1971 | Borodkin et al. . |
| 4,152,493 | 5/1979 | Yotsumoto et al. . |
| 4,172,120 | 10/1979 | Todd et al. . |
| 4,221,778 | 9/1980 | Raghunathan . |
| 4,252,790 | 2/1981 | Higuchi . |
| 4,358,546 | 11/1982 | Naomi et al. . |
| 4,374,932 | 2/1983 | Pitzele et al. . |
| 4,423,158 | 12/1983 | Porath . |
| 4,436,738 | 3/1984 | Bequette et al. . |
| 4,448,774 | 5/1984 | Clemente et al. ...................... 424/243 |
| 4,459,278 | 7/1984 | Porter . |
| 4,578,268 | 3/1986 | Quinlan . |
| 4,593,073 | 6/1986 | St-Pierre et al. . |
| 4,692,462 | 9/1987 | Banerjee . |
| 4,762,709 | 8/1988 | Sheumaker ............................ 424/78.1 |
| 4,780,322 | 10/1988 | Martani et al. . |
| 4,788,055 | 11/1988 | Fischer et al. . |
| 4,847,077 | 7/1989 | Raghunathan . |
| 4,859,461 | 8/1989 | Chow et al. . |
| 4,859,462 | 8/1989 | Chow et al. . |
| 4,894,239 | 1/1990 | Nonomura et al. . |
| 4,973,607 | 11/1990 | Stahlbush et al. . |
| 4,996,047 | 2/1991 | Kelleher et al. ....................... 424/78.1 |
| 4,999,189 | 3/1991 | Kogan et al. . |
| 5,032,393 | 7/1991 | Douglas et al. . |
| 5,071,646 | 12/1991 | Malkowska et al. . |
| 5,108,733 | 4/1992 | Frontini et al. . |
| 5,141,966 | 8/1992 | Porath . |
| 5,152,986 | 10/1992 | Lange et al. . |
| 5,177,076 | 1/1993 | Nijkerk et al. . |
| 5,182,102 | 1/1993 | DeSantis, Jr. et al. . |
| 5,186,930 | 2/1993 | Kogan et al. . |
| 5,188,825 | 2/1993 | Iles et al. . |
| 5,200,473 | 4/1993 | Jeanneret-Gris . |
| 5,217,954 | 6/1993 | Foster et al. . |
| 5,288,503 | 2/1994 | Wood et al. . |
| 5,334,378 | 8/1994 | Mitani et al. . |
| 5,338,532 | 8/1994 | Tomalia et al. . |
| 5,350,584 | 9/1994 | McClelland et al. . |
| 5,368,852 | 11/1994 | Umemoto et al. ..................... 424/78.1 |
| 5,413,782 | 5/1995 | Warchol et al. . |
| 5,453,429 | 9/1995 | Bliem et al. . |
| 5,540,918 | 7/1996 | Castillo et al. . |
| 5,575,993 | 11/1996 | Ward et al. . |

FOREIGN PATENT DOCUMENTS

| | | | |
|---|---|---|---|
| 4640351 | 11/1971 | Japan ................................ | 424/78.1 |

OTHER PUBLICATIONS

Packaging for Delsym® DM Controlled–Release Dextromethorphan Polystirex Suspension, Ciba Self Medication, Mississanga, Ontario, Jan. 31, 1996.

*Primary Examiner*—Peter F. Kulkosky
*Attorney, Agent, or Firm*—Popovich & Wiles, P.A.

[57] ABSTRACT

The invention provides a pharmaceutical composition comprising a drug-resin complex and a chelating agent in which the composition is in the form of a solid or a gel. The invention also provides a method of making such a composition and a method for improving the stability of a pharmaceutical composition.

37 Claims, No Drawings

DRUG-RESIN COMPLEXES STABILIZED BY CHELATING AGENTS

FIELD OF THE INVENTION

The present invention relates generally to pharmaceutical compositions. The invention particularly relates to drug-resin complexes stabilized by chelating agents and a method of making these drug-resin complexes. Another aspect of the invention is a method for using such stabilized drug-resin complexes in the treatment of patients.

BACKGROUND OF THE INVENTION

The reaction or complexation of a drug with an ion exchange resin forms a composition known as a drug-resin complex. A drug for the purposes of the present invention is a medicinal substance for internal or external use. An ion exchange resin is an ionic, or charged, compound which has binding sites that can bind or take up an ionic drug. The most common types of ion exchange resins are polymers. Such a compound is called a resin because the polymer is formed into very small particles or beads.

Drug-resin complexes have several advantages over pure drugs in ordinary formulations. Many drugs are bitter and some smell bad. Getting a patient, particularly a small child or an elderly person, to swallow something that tastes or smells bad can be a serious problem. Complexing such a drug with a resin often improves the taste or the smell.

Complexing a drug with a resin can also change its physical characteristics. This change may make the drug more convenient to mass produce or easier for patients to take. For example, mixing a drug in powder form with inert ingredients and compressing the mixture into a tablet is a very common and inexpensive way of preparing a drug for consumption. However, if a particular drug in liquid or powder form tends to make a crumbly or sticky mixture, large-scale automated tablet compression may be impossible or overly costly. Complexing a drug with a resin can sometimes improve compression characteristics.

Complexing a drug with a resin can affect the rate at which the drug dissolves in the digestive system of a patient. Fast dissolution can be a problem if it means the drug has to be taken often to maintain a reasonably even level of the drug in the blood. If a drug causes stomach upset when it dissolves, rapid dissolution in the stomach may also be undesirable. Drug-resin complexes often dissolve more slowly than an ordinary drug formulation. Complexes are useful in changing dissolution profiles and are frequently used in time-release formulations. Coating of a drug-resin complex can delay the release of a drug even more.

The technique for adsorption of a drug onto an ion exchange resin to form a drug-resin complex is well-known. Generally the drug is mixed with an aqueous suspension of the ion exchange resin and the complex is dried. Complexation of the drug by the resin may be detected by a change in pH or by other changes in physical properties or by a decrease in concentration of drug dissolved in the aqueous phase.

Ion exchange resins are usually made from a polymer backbone with various displaceable functional groups ionically bonded to the polymer. In water the functional groups of the resin ionize. The polymer chains are also typically cross linked, leading to a gel-like insoluble composition formed in beads. The particle size of a resin can differ between two resins even though the polymer it is made from is the same. The amount of cross linking also varies from one resin to another. The amount of drug which can be bound to a particular resin is called its binding capacity or loading. Binding capacity varies greatly between resins and from drug to drug. Most resins are sold in dehydrated form and then soaked in water prior to use.

Cationic ion exchange resins have negatively charged, or anionic, binding sites. The anionic binding sites are bonded to displaceable cationic groups. Cationic drugs are positively charged and tend to displace the cationic groups, typically becoming bonded to the resin by ionic bonds. Since basic drugs are generally cationic, cationic exchange resins are often used to prepare drug-resin complexes with basic drugs. Typical approaches to forming a water insoluble drug-resin complex are to react the sodium salt of a cationic ion exchange resin with a cationic drug or to react the base form of the drug with the acid form of the cationic ion exchange resume.

Anionic ion exchange resins have positively charged, or cationic, binding sites. The cationic binding sites are bonded to displaceable anionic groups. Anionic drugs are negatively charged and tend to displace the anionic groups, typically becoming bonded to the resin by ionic bonds. Since acidic drugs are generally anionic, anionic exchange resins are frequently used to prepare drug-resin complexes for acidic drugs. Once a drug-resin complex reaches the digestive system of a patient, the many ions present there tend in turn to displace the drug from the resin and release the drug.

Many drugs have been found to be chemically unstable when reacted with a resin. The drug alone does not degrade in the same way. The decomposition products generally are oxidized forms of the drug, or in some cases hydrolytic products. This decomposition occurs both in the presence of water and when the drug-resin complex is dry. U.S. Pat. No. 5,413,782 (Warchol et al.) describes a method for increasing take-up of the drug and preventing decomposition of anionic drug-ion exchange resin systems. This method involves, not adding a chemical, but rather reacting the drug and the resin in the absence of carbon dioxide and/or bicarbonate ion.

The use of chelating agents to stabilize chemicals and drugs in solution is known. Chelating agents are scavengers for trace amounts of metal ions. Chelation refers to the formation of an unusually stable bond between an organic compound and an ion or other polar group. Most commonly chelation involves a metal ion. The unusual stability of the bond is due to the ability of the organic compound to bind to a central ion at two or more binding sites, often in a ring formation. Compounds which have this ability are known as chelating agents or chelating ligands. The resulting combination of a chelating ligand with a metal ion is referred to as a metal complex. Many reactions, including many oxidation and decomposition reactions, are catalyzed by trace amounts of metallic ions present in solutions. Many drugs can be degraded through oxidation and hydrolytic reactions which are catalyzed by metal ions. The presence of metallic ions can therefore significantly accelerate the degradation of these drugs. Chelating agents are useful in preventing degradation for drugs in solution. EDTA (ethylene diamine tetraacetic acid) and its salts are examples of powerful chelating agents. EDTA is known to stabilize drugs in solution by retarding their oxidation.

U.S. Pat. No. 4,973,607 (Stahlbush et al.) describes the use of antioxidants to improve the chemical stability of cationic exchange resins. This differs from the present invention in that only the resin is involved, not a drug-resin complex. U.S. Pat. No. 4,221,778 (Raghunathan) describes prolonged release pharmaceutical preparations made of ion exchange resin drug complexes treated with a solvating agent and provided with a diffusion barrier coating.

U.S. Pat. No. 5,368,852 (Umemoto et al.) describes prolonged release liquid pharmaceutical preparations of drug-resin complexes coated with ethylcellulose and including a benzoate preservative to reduce bacterial activity. U.S. Pat. Nos. 5,182,102 (DeSantis, Jr. et al.) and 5,540,918 (Castillo et al.) describe drug-resin ophthalmic compositions whose resistance to bacterial contamination is improved by the use of antimicrobials. EDTA is disclosed as an antimicrobial in such compositions.

U.S. Pat. No. 4,894,239 (Nonomura et al.) discloses preparations that contain drug-resin complexes in which an antioxidant may be added. U.S. Pat. No. 5,152,986 (Lange et al.) also discloses preparations that contain drug-resin complexes in which an antioxidant may be added.

U.S. Pat. No. 4,448,774 (Clemente et al.) discloses aqueous pharmaceutical solutions that contain a drug, a pharmaceutically acceptable preservative such as sodium benzoate, and a chelating agent such as ethylene diamine tetraacetic acid. None of the patents described above discloses a pharmaceutical composition in the form of a solid or gel that comprises a drug-resin complex and a chelating agent.

SUMMARY OF THE INVENTION

The invention provides a pharmaceutical composition comprising a drug-resin complex and a chelating agent, in which the composition is in the form of a solid or a gel.

The invention also provides a method of making a pharmaceutical composition comprising: (a) combining a drug and an ion exchange resin in a liquid to form a drug-resin complex; (b) adding a chelating agent; and (c) drying the result of step (b) to form a solid or gel pharmaceutical composition. The invention also provides a pharmaceutical composition prepared by this method.

The invention also provides a method for improving the stability of a pharmaceutical composition that contains a drug-resin complex comprising adding a chelating agent in an amount effective to reduce the rate of degradation of the drug in the drug-resin complex.

Additional features and advantages of the invention are set forth in the description which follows and in part will be apparent from the description. The objectives and other advantages of the invention will be realized and attained by the drug-resin complexes stabilized by chelating agents and their uses as particularly pointed out in the written description and claims.

It is to be understood that both the foregoing general description and the following detailed description are exemplary and explanatory and are intended to provide further explanation of the invention as claimed.

DESCRIPTION OF THE PREFERRED EMBODIMENTS

The present invention provides a method of using chelating agents to stabilize drugs which have been taken up by resins and, in particular, ion exchange resins. The drugs are not in solution, but rather present in the form of a drug-resin complex. The drug may be any of a wide variety of drugs suitable for the formation of a drug-resin complex and subject to degradation after complexation. The ion exchange resin may be any non-toxic ion exchange resin. The chelating agent may be added during the formation of the complex, after its formation, or at any time during the process. The stabilization is effective either when the complex is dry or when the complex is suspended in water. The complex may be coated or uncoated as necessary to obtain a desirable dissolution profile. Solvating agents may be used in the process to prevent the resin particles from breaking and to aid in the application of coatings. It should be noted that resins such as amphoteric resins and other neutral resins may also be used in the practice of the present invention as long as the binding, complexation, or adsorption of the drug into the resin is sufficient.

The stabilization of a drug-resin complex by a chelating agent involves reacting a resin with a drug to form the drug-resin complex and adding the chelating agent to the complex. These two steps may occur in any order or may be simultaneous. Additional steps may be included in the procedure, such as adding a solvating agent or a coating. These steps may also occur in any order. The complex is dried before use, but it may be suspended in liquid again later.

The invention also provides a pharmaceutical composition comprising a drug-resin complex and a chelating agent, wherein the composition is in the form of a solid or a gel. Without the chelating agent, the complexed drug would be degraded by oxidation reactions or hydrolytic reactions catalyzed by metal ions. The drug to be complexed may be chosen because of some undesirable property of the uncomplexed drug, such as unpleasant taste or odor, or poor compression or dissolution characteristics. The drug in the drug-resin complex can be a basic, acidic, or amphoteric drug. The drug can be a basic drug selected from dextromethorphan, codeine, morphine, hydrocodone, pseudoephedrine, or phenylpropanolamine.

The resin in the drug-resin complex can be a cationic exchange resin. In a preferred embodiment, the resin is a gel type divinylbenzene sulfonic acid cationic exchange resin, and when using this resin the drug is preferably a basic drug. The resin in the drug-resin complex can be an anionic exchange resin, and when using this type of resin, the drug in the drug-resin complex is preferably an acidic drug.

The chelating agent preferably is selected from EDTA, a salt of EDTA, desferrioxamine B, deferoxamine, dithiocarb sodium, penicillamine, pentetate calcium, a sodium salt of pentetic acid, succimer, trientine, nitrilotriacetic acid, trans-diaminocyclohexanetetraacetic acid (DCTA), diethylenetriaminepentaacetic acid, bis(aminoethyl)glycolether-N,N,N', N'-tetraacetic acid, iminodiacetic acid, citric acid, tartaric acid, fumaric acid, or a salt thereof. More preferably, the chelating agent is selected from EDTA or a salt of EDTA. Most preferably the chelating agent is disodium edetate, which is contacted with the drug-resin complex in a solution containing sufficient sodium hydroxide to form a significant amount of tetrasodium edetate in solution.

In one embodiment, the chelating agent is not covalently bound to the drug resin complex. In another embodiment, the chelating agent is covalently bound to the drug resin complex. The chelating agent can be present in a concentration of from 0.001 percent to 10 percent by weight, more preferably from 0.1 to 5 percent by weight. Most preferably, the concentration of the chelating agent is about 0.3 to 0.4 percent by weight for a solid dosage form. For a dosage form which is a suspension, the concentration of the chelating agent is most preferably about 0.05% by weight.

The chelating agent preferably is present in an amount effective to reduce the rate of degradation of the drug in the drug-resin complex. The rate of degradation of a drug in a drug-resin complex depends on the particular drug and resin and other factors such as storage temperature. The rate of degradation is preferably as low as possible. In a preferred embodiment, the chelating agent is present in an amount effective to reduce the amount of degradation of the drug in the drug resin complex by more than 20 percent over twelve months of storage at room temperature relative to an otherwise identical pharmaceutical composition without the chelating agent. For instance, if two samples of a drug-resin complex, one treated with chelating agent and one untreated, each had 20 percent by weight of drug at the beginning of the twelve month period, and the untreated sample had 18 percent by weight of drug after the end of the 12 month period of storage at room temperature, then 2 percent by weight of the drug degraded in the untreated sample. Then preferably, the amount of degradation of the drug in the drug-resin complex treated with chelating agent after the 12 month period of storage at room temperature will be reduced by more than 20 percent, i.e., instead of 2 percent by weight of degradation, less than 1.6 percent by weight of degradation.

The drug-resin complex can comprise a diffusion barrier coating, in a preferred embodiment the diffusion barrier coating is an enteric coating. The diffusion barrier coating improves the dissolution characteristics of the drug-resin complex. The drug-resin complex preferably comprises a solvating agent, and the solvating agent preferably is polyethylene glycol. In a preferred embodiment, the drug-resin complex comprises a solvating agent and a diffusion barrier coating. In another preferred embodiment, the resin in the drug-resin complex is a divinylbenzene sulfonic acid cationic exchange resin, the drug is a basic drug, and the chelating agent is EDTA or a salt of EDTA.

The pharmaceutical composition is suitable for oral, topical, rectal, vaginal, nasal, or ophthalmic administration. The pharmaceutical composition can be in the form of a tablet, a capsule, a powder, a lotion, a cream, or a suppository. In a preferred embodiment, the pharmaceutical composition is suitable for oral administration.

The invention also provides a method of making a pharmaceutical composition comprising: (a) combining a drug and an ion exchange resin in a liquid to form a drug-resin complex; (b) adding a chelating agent; and (c) drying the result of step (b) to form a solid or gel pharmaceutical composition. Preferably the chelating agent is present in an amount effective to reduce the rate of degradation of the drug in the drug-resin complex.

The invention also provides a method of making a pharmaceutical composition comprising: (a) combining a drug and an ion exchange resin in a liquid to form a drug-resin complex; (b) adding a chelating agent; (c) drying the result of step (b) to form a solid; and (d) suspending the result of step (c) in an appropriate liquid to form a liquid pharmaceutical composition.

The invention provides a method of making a pharmaceutical composition comprising: (a) combining a drug and an ion exchange resin in a first liquid to form a drug-resin complex; (b) drying the result of step (a) to form a solid; (c) suspending the result of step (b) in an appropriate second liquid, which may be the same or different than the first liquid; and (d) adding a chelating agent, to form a liquid pharmaceutical composition.

The invention also provides a pharmaceutical composition prepared by the process of: (a) combining a drug and an ion exchange resin in a liquid to form a drug-resin complex; (b) adding a chelating agent; and (c) drying the result of step (b) to form a solid or gel pharmaceutical composition.

The invention further provides a pharmaceutical composition prepared by the process of: (a) combining a drug and an ion exchange resin in a liquid to form a drug-resin complex; (b) adding a chelating agent; (c) drying the result of step (b) to form a solid; and (d) suspending the result of step (c) in an appropriate liquid to form a liquid pharmaceutical composition.

The invention also provides a pharmaceutical composition prepared by the process of: (a) combining a drug and an ion exchange resin in a first liquid to form a drug-resin complex; (b) drying the result of step (a) to form a solid; (c) suspending the result of step (b) in an appropriate second liquid, which may be the same or different than the first liquid; and (d) adding a chelating agent, to form a liquid pharmaceutical composition.

The invention provides a method for improving the stability of a pharmaceutical composition that contains a drug-resin complex comprising adding a chelating agent in an amount effective to reduce the rate of degradation of the drug in the drug-resin complex. The composition may be a solid, gel, or suspension. The chelating agent preferably is present in an amount effective to reduce the rate of degradation of the drug in the drug-resin complex by 20 percent over twelve months of storage at room temperature relative to an otherwise identical pharmaceutical composition without the chelating agent. In a preferred embodiment, the agent is present in an amount effective to reduce the rate of degradation of the drug in the drug-resin complex by 30 percent over twelve months of storage at room temperature, and in another preferred embodiment, the agent is present in an amount effective to reduce the rate of degradation of the drug in the drug-resin complex by 50 percent over twelve months of storage at room temperature.

The invention also provides a method for administering a drug to a patient in need thereof, comprising: (a) providing a pharmaceutical composition that contains a drug-resin complex that contains the drug; (b) adding a chelating agent; (c) storing the combination of step (b); and (d) subsequently administering the combination of step (b) to the patient. The chelating agent preferably is present in an amount effective to reduce the rate of degradation of the drug in the drug-resin complex.

Many different resins may be successfully used. The ion exchange resin chosen should not be toxic to humans and generally should not have any medicinal effect by itself. Ion exchange resins known to be useful in the present invention are AMBERLITE IRP-69 and AMBERLITE IRP-70 (both available from Rohm & Haas). These two resins are gel type divinylbenzene sulfonic acid cationic exchange resins. IRP-69 and IRP-70 resins are chemically identical but differ in particle size. Both cationic and anionic exchange resins may be used for the invention. Suitable resins for the practice of the invention include functionalized resins derived from divinylbenzenes, trivinylbenzenes, styrenic, methacrylic, methacrylamide, acrylic, acrylamide, carbacrylic, phenol-formaldehyde, polyhydroxy resins, polycarboxylic, carboxyvinyl, cellulosic, and dextran polymer resins. Also suitable for the invention are inorganic ion exchange resins such as zeolite, fuller's earth, peat, lignite, permutite, dolomite, iron oxide hydrate gel, zirconium oxide hydrate gel, and activated carbon. Amphoteric resins, i.e, those derived from the above monomers but containing both anionic and cationic sites in the same polymer may also be used. Zwitterinonic resins may also be used in the practice of the present invention.

When sulfonic acid cationic exchange resins are used, their particle size is typically in the range of about 25 to about 1000 μm. Many of the illustrative examples employ AMBERLITE® IRP-70 resin, a cationic exchange resin which is 100–200 mesh (75–150 μm) fractured resin particles of AMBERLITE IR-120. The parent resin of AMBERLITE IR-120 and IR-70 is described by the manufacturer as a gel-type divinylbenzene sulfonic acid cationic exchange resin which swells in water with a pH range of 0 to 14.

All drugs which exist in ionic form in a semi-polar or polar solvent, such as water, are potential candidates for use in the present invention. All acidic and basic drugs are suitable. Examples include drugs having basic groups such as amino groups, hydrazino groups, amidino groups, guanidino groups, and heterocyclic groups containing nitrogen. Additional examples include drugs which are carboxylic acids or amides, or which have carbonyl groups or other acidic groups.

A large percentage of the available pharmaceutically active compounds are capable of forming complexes with ion exchange resins. Stabilization of a drug-resin complex by EDTA is known to be effective for the drugs dextromethorphan, codeine, morphine, hydrocodone, and phenylpropanolamine. Stabilization is also effective for pseudoephedrine, dihydrocodeine, salts and derivatives of morphine, methylephedrine, ephedrin, paraamino salicylic acid, acetyl salicylic acid, phentermine, acetaminophen, pilocarpine, metoclopramide, theophylline, and ibuprofen. Other possible drugs for use in the invention include all alpha-adrenergic agonists and blockers; beta-adrenergic agonists and blockers; narcotic and non-narcotic analgesics; anorexics; antiallergics; antiamebics; antianginals; antiasthmatics; antibacterials such as aminoglycosides, carbacephems, carbapenems, cephalosporins, cephamycins, penicillins, polypeptides, tetracyclines, quinolones, and sulfonamides; anticholinergics; antidepressants; antifungals; nonsteroidal anti-inflammatories; antispasmodics; antiulceratives; antivirals; anxiolytics; calcium channel blockers; dopamine receptor agonists and antagonists; narcotic antagonists; protease inhibitors; respiratory stimulants; retroviral protease inhibitors; reverse transcriptase inhibitors; sedatives such as benzodiazepine derivatives; and cerebral, coronary, and peripheral vasodilators. Of course, depending on the $pK_a$ of the drug, either an anionic or cationic exchange resin will be selected. In some cases an amphoteric resin may be used depending on the physicochemical properties of the drugs, i.e., $pK_a$ as well as binding constants.

Suitable examples of the above families of drugs for use in the present invention include the following.

Alpha-adrenergic agonists that can be used include adrafinil, adrenolone, amidephrine, apraclonidine, budralazine, clonidine, cyclopentamine, detomidine, dimetofrine, dipivefrin, ephedrine, epinephrine, fenoxazoline, guanabenz, guanfacine, hydroxyamphetamine, ibopamine, indanazoline, isometheptene, mephentermine, metaraminol, methoxamine, methylhexaneamine, metizoline, midodrine, modafinil, moxonidine, naphazoline, norepinephrine, norfenefrine, octodrine, octopamine, oxymetazoline, phenylephrine hydrochloride, phenylpropanolamine hydrochloride, phenylpropyl-methylamine, pholedrine, propylhexedrine, pseudoephedrine, rilmenidine, synephrine, talipexole, tetrahydrozoline, tiamenidine, tramazoline, tuaminoheptane, tymazoline, tyramine, and xylometazoline.

Beta-adrenergic agonists that can be used include albuterol, bambuterol, bitolterol, carbuterol, clenbuterol, clorprenaline, denopamine, dioxethedrine, dopexamine, ephedrine, epinephrine, etafedrine, ethylnorepinephrine, fenoterol, formoterol, hexoprenaline, ibopamine, isoetharine, isoproterenol, mabuterol, metaproterenol, ethoxyphenamine, oxyfedrine, pirbuterol, prenalterol, procaterol, protokylol, reproterol, rimiterol, ritodrine, salmeterol, soterenol, terbutaline, tretoquinol, tulobuterol, and xamoterol.

Alpha-adrenergic blockers that can be used include amosulalol, rotinolol, dapiprazole, doxazosin, ergoloid mesylates, fenspiride, indoramin, labetalol, naftopidil, nicergoline, prazosin, tamsulosin, terazosin, tolazoline, trimazosin, and yohimbine.

Beta-adrenergic blockers that can be used include acebutolol, alprenolol, amosulalol, arotinolol, atenolol, befimolol, betaxolol, bevantolol, bisoprolol, bopindolol, bucumolol, bufetolol, bufuralol, bunitrolol, bupranolol, butidrine hydrochloride, butofilol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfmalol, talinolol, tertatolol, tilisolol, timolol, toliprolol, and xibenolol.

Narcotic analgesics that can be used include alfentanil, benzylmorphine, codeine, codeine methyl bromide, codeine phosphate, codeine sulfate, desomorphine, dihydrocodeine, dihydrocodeinone enol acetate, dihydromorphine, ethylmorphine, hydrocodone, hydromorphone, methadone hydrochloride, morphine, morphine hydrochloride, morphine sulfate, nicomorphine, normethadone, normorphine, opium, oxycodone, oxymorphone, phenoperidine, and propiram.

Non-narcotic analgesics that can be used include aceclofenac, acetaminophen, acetanilide, acetylsalicylsalicylic acid, aspirin, carbamazepine, dihydroxyaluminum acetylsalicylate, fenoprofen, fluproquazone, ibufenac, indomethacin, ketorolac, magnesium acetylsalicylate, morpholine salicylate, naproxen, phenacetin, phenyl salicylate, salacetamide, salicin, salicylamide, sodium salicylate, and tolfenamic acid.

Anorexics that may be used include aminorex, amphecloral, amphetamine, benzphetamine, chlorphentermine, clobenzorex, cloforex, clortermine, cyclexedrine, dextroamphetamine sulfate, diethylpropion, diphemethoxidine, n-ethylamphetamine, fenbutrazate, fenfluramine, fenproporex, furfurylmethyl amphetamine, levophacetoperane, mazindol, mefenorex, metamfepramone, metharnphetamine, norpseudoephedrine, pentorex, phendimetrazine, phenmetrazine, phentermine, phenylpropanolamine hydrochloride, picilorex, and sibutramine.

Antiallergics that may be used include amlexanox, astemizole, azelastine, cromolyn, fenpiprane, ibudilast, lodoxamide, nedocromil, oxatomide pemirolast, pentigetide, picumast, repirinast, suplatast tosylate, tazanolast, tranilast, and traxanox.

Antianginals that can be used include acebutolol, alprenolol, amiodarone, amlodipine, arotinolol, atenolol, barnidipine, bepridil, bevantolol, bucumolol, bufetolol, bufuralol, bunitrolol, bupranolol, carazolol, carteolol, celiprolol, cinepazet maleate, diltiazem, elgodipine, epanolol, felodipine, gallopamil, imolamine, indenolol, isosorbide dinitrate, sradipine, limaprost, mepindolol, metoprolol, molsidomine, nadolol, nicardipine, nicorandil, nifedipine, nifenalol, nilvadipine, nipradilol, nisoldipine, nitroglycerin, oxprenolol, oxyfedrine, ozagrel, penbutolol, pentaerythritol tetranitrate, pindolol, pronethalol, propranolol, ranolzazine, somotiadil, sotalol, terodiline, timolol, toliprolol, trolnitrate phosphate, verapimil, and zatebradine.

Antiasthmatics that can be used include amlexanox, azelastine, cromolyn, ibudilast, ketotifen, montelukast, nedocromil, oxatomide, pranlukast, seratrodast, suplatast tosylate, tiaramide, traxanox, zafirlukast, and zileuton.

Antibacterials or antibiotics can be used. The general classes of aminoglycosides, carbacephems, carbapenems, cephalosporins, cephamycins, penicillins, polypeptides, tetracyclines, etc. can be used. Specific antibacterials or antibiotics that can be used include arnikacin, dihydrostreptomycin, kanamycin, neomycin, neomycin undecylenate, spectinomycin, streptomycin, loracarbef, biapenem, cefaclor, cefazolin, cefepime, cephalosporin C, cefbuperazone, andinocillin, amoxicillin, ampicillin, cloxacillin, metampicillin, penicillin G benzathine, penicillin G procaine, penicillin V, piperacillin, amphomycin, vancomycin, viomycin, apicycline, chlortetracycline, methacycline, and tetracycline.

Synthetic antibacterials such as quinolones and analogs, sulfonamides, etc. can be used. Specific synthetic antibacterials that can be used include cinoxacin, lomefloxacin, nalidixic acid, oxolinic acid, acetyl sulfa -methoxypyrazine, mafenide, succinylsulfathiazole, sulfacetamide, sulfadiazine, and sulfaloxic acid.

Anticholinergics that can be used include adiphenine hydrochloride, aminopentamide, atropine, chlorphenoxamine, cyclodrine, mecloxamine pentapiperide, phencarbamide, pridinol, and scopolamine.

Antidepressants that can be used include bicyclics, hydrazides, hydrazines, pyrrolidones, tetracyclics, tricyclics, etc. Specific antidepressants that can be used include binedaline, nefopam, trazodone, iproniazid, rolipram, maprotiline, adinazolam, amitriptyline, clomipramine, imipramine, nortriptyline, primipramine, adrafinil, milnacipran, nefazodone, and zimeldine.

Synthetic antifungals that can be used include allylamines, imidazoles, thiocarbamates, triazoles, etc. Specific synthetic antifingals that can be used include butenafme, bifonazole, butoconazole, chlordantoin, clotrimazole, tolciclate, fluconazole, acrisorcin, exalamide, triacetin, and zinc propionate. Nonsteroidal anti-inflammatories that can be used include aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, etc. Specific nonsteroidal anti-inflammatories that can be used include flufenamic acid, terofenamate, acemetacin, clopirac indomethacin, metiazinic acid, fenbufen, clidanac, alminoprofen, bucloxic acid, ketoprofen, naproxen, tiaprofenic acid, difenamizole, apazone, mofebutazone, phenylbutazone, acetaminosalol, lysine acetylsalicylate, parsalmide, ampiroxicam, bendazac, nabumetone, superoxide dismutase, and zileuton.

Antispasmodics that can be used include alibendol, ambucetamide, aminopromazine, apoatropine, bevonium methyl sulfate, bietamiverine, butaverine, butropium bromide, caroverine, cimetropium bromide, cinnamedrine, clebopride, cyclonium iodide, difemerine, diisopromine, dioxaphetyl butyrate, diponium bromide, drofenine, emepronium bromide, fenalamide, fenoverine, flavoxate, flopropione, gluconic acid, hydramitrazine, hymecromone, octamylamine, pentapiperide, phloroglucinol, pinaverium bromide, piperilate, prifinium bromide, proxazole, racefimine, rociverine, spasmolytol, sultroponium, tigloidine, tiropramide, tricromyl, trimebutine, and xenytropium bromide.

Antiulceratives that can be used include acetoxolone, aldioxa, arbaprostil, benexate hydrochloride, carbenoxolone, cetraxate, cimetidine, colloidal bismuth subcitrate, ebrotidine, ecabet, enprostil, esaprazole, famotidine, gefarnate, guaiazulene, irsogladine, lansoprazole, misoprostol, nizatidine, omeprazole, ornoprostil, pantoprazole, pifarnine, pirenzepine, plaunotol, polaprezinc, rabeprazole, ranitidine, rebamipide, rioprostil, rosaprostol, rotraxate, roxatidine acetate, sofalcone, spizofurone, sucralfate, telenzepine, teprenone, trimoprostil, trithiozine, troxipide, and zolimidine.

Antivirals such as purines, pyrimidines, etc. can be used. Specific antivirals that can be used include acyclovir, cidofivir, cytarabine, dideoxyadenosine, didanosine, edoxudine, famciclovir, floxuridine, ganciclovir, idoxuridine, inosine pranobex, lamivudine, penciclovir, sorivudine, stavudine, zidovudine, acemannan, amantadine, amidinomycin, lysozyme, nevirapine, and ribavirin.

Anxiolytics such as arylpiperazines, benzodiazepine derivatives, carbamates, etc. can be used. Specific anxiolytics that can be used include buspirone, lesopitron, alprazolam, bromazepam, diazepam, fludiazepam, loxapine, metaclazepam, prazepam, cyclarbamate, meprobamate, abecarnil, benzoctamine, glutamic acid, mephenoxalone, and pazinaclone.

Calcium channel blockers such as arylalkylamines, dihydropyridine derivatives, piperazine derivatives, etc. can be used. Specific calcuim channel blockers that can be used include bepridil, diltiazem, gallopamil, terodiline, amlodipine, benidipine, lercanidipine, nicardipine, cinnarizine, and fantofarone.

Dopamine receptor agonists can be used. Specific dopamine receptors that can be used include bromocriptine, cabergoline, camioxirole, dopexamine, fenoldopam, ibopamine, lisuride, pergolide, pramipexole, quinagolide, ropinirole, roxindole, and talipexole. Dopamine receptor antagonists can be used. Specific dopamine receptor antagonists that can be used include amisulpride, clebopride, domperidone, metoclopramide, mosapramine, nemonapride, romoxipride, risperidone, sulpiride, sultopride, and ziprasidone.

Narcotic antagonists can be used. Specific narcotic anagonists that can be used include amiphenazole, cyclazocine, levallorphan, nalmefene, nalorphine, naloxone, and naltrexone.

Protease inhibitors can be used. Specific protease inhibitors that can be used include aprotinin, camostat, gabexate, nafamostat, and urinastatin.

Respiratory stimulants can be used. Specific respiratory stimulants that can be used include ahnitrine, bemegride, cropropamide, crotethamide, dimefline, dimorpholamine, doxapram, ethamivan, fominoben, lobeline, mepixanox, nikethamide, picrotoxin, pimeclone, pyridofylline, sodium succinate, and tacrine.

Retroviral protease inhibitors can be used. Specific retroviral protease inhibitors that can be used include indinavir, and ritonavir.

Reverse transcriptase inhibitors can be used. Specific reverse transcriptase inhibitors that can be used include delavirdine, didanosine, dideoxyadenosine, foscarnet sodium, lamivudine, nevirapine, stavudine, suramin sodium, zalcitabine, and zidovudine.

Sedatives such as benzodiazepine derivatives can be used. Specific sedatuves that can be used include brotizolam, cinolazepam, doxefazepam, estazolam, flunitrazepam, flurazepam, haloxazolam, loprazolam, lormetazepam, nitrazepam, quazepam, temazepam, and triazolam.

Cerebral vasodilators can be used. Specific cerebral vasodilators that can be used include bencyclane, cinnarizine, citicoline, cyclandelate, ciclonicate, eburnamonine, fasudil, fenoxedil, flunarizine, ibudilast, ifenprodil, lomerizine, nafronyl, nicametate, nicergoline, nimodipine, papaverine, pentifylline, tinofedrine, vincamine, vinpocetine, and viquidil.

Coronary vasodilator can be used. Specific coronary vasodilators that can be used include amotriphene, bendazol, benfurodil hemisuccinate, benziodarone, chloracizine, chromonar, clobenfurol, clonitrate, cloricromen, dilazep, dipyridamole, droprenilamine, efloxate, erytlirityl tetranitrate, etafenone, fendiline, floredil, ganglefene, heart muscle extract, hexobendine, itramin tosylate, khellin, lidoflazine, mannitol hexanitrate, medibazine, pentaerythritol tetranitrate, pentrinitrol, perhexiline, pimefylline, prenylamine, propatyl nitrate, pyridofylline, trapidil, tricromyl, trimetazidine, trolnitrate phosphate, and visnadine.

Peripheral vasodilator can be used. Specific peripheral vasodilators that can be used include bamethan, bencyclane, betahistine, bradykinin, brovincamine, bufeniode, buflomedil, butalamine, cetiedil, ciclonicate, cmepazide, cyclandelate, eledoisin, fenoxedil, flunarizine, hepronicate, ifenprodil, iloprost, inositol niacinate, isoxsuprine, kallidin, kallikrein, moxisylvyte, nafronyl, nicametate, nicergoline, nicofuranose, nicotinyl alcohol, nylidrin, pentifylline, pentoxifylline, piribedil, suloctidil, tolazoline, and xanthinol niacinate.

Antiamebics that can be used include arstiinol, bialamicol, carbarsone, cephaeline, chlorbetamide, chloroquine, chlorphenoxamide, chlortetracycline, dehydroemetine, dibromopropamidine, diloxanide, diphetarsone, emetine, fumagillin, glaucarubin, iodoquinol, paromomycin, phanquinone, polybenzarsol, propamidine, quinfamide, secnidazole, sulfarside, teclozan, tetracycline, thiocarbamizine, thiocarbarsone, and tinidazole.

Adsorption of the drug onto the resin particles, i.e., ion exchange resin particles to form the drug resin complex is a well known technique as shown in U.S. Pat. Nos. 2,990,332 (Keating) and 4,221,778 (Raghunathan). In general, the drug is mixed with an aqueous suspension of the resin, and the complex is then washed and dried. Adsorption of drug onto the resin may be detected by a change in the pH of the reaction medium or by a reduction in the concentration of dissolved drug in the reaction solvent. Again, the $pK_a$ of the drug will determine the type of resin which can be used. Generally the loading of the drug on the resin particles can be from about 1 to about 90 percent by weight, although 15 to 50 percent by weight is in the normal practical range.

Several different chelating agents are useful in stabilizing drug-resin complexes. However, the chelating agent is preferably EDTA or one of the salts of EDTA. More than one type of chelating agent may be used with a particular drug-resin complex. The amount of chelating agent should be an amount effective to reduce the rate of degradation of the drug in the drug-resin complex. The appropriate amount of chelating agent easily can be determined by experiment. Salts of EDTA include edetate calcium disodium, edetate trisodium, edetate disodium, and edetate sodium. EDTA and its salts have been found to inhibit the oxidation of drug-resin complexes. Stabilization by EDTA takes place both in the absence of water and when the drug-resin or coated drug-resin is suspended in water. Other useful chelating agents include desferrioxamine B, deferoxamine, dithiocarb sodium, penicillamine, pentetate calcium, sodium salts of pentetic acid, succimer, trientine, nitrilotriacetic acid, trans-diaminocyclohexanetetraacetic acid (DCTA), diethylenetri-aminepentaacetic acid, bis(aminoethyl)glycolether-N,N,N', N'-tetraacetic acid, iminodiacetic acid, citric acid, tartaric acid, fumaric acid, or a salt thereof. Preferably the chelating agent is inexpensive and stable, and forms strong metal complexes with a wide variety of metal ions. In addition it is desirable for the chelating agent to be completely non toxic and to have no pharmacological effect on the body except for its chelating effect. Synthetic multidentate aminocarboxylic acids, such as EDTA, bind metals strongly and are useful chelators for the practice of the invention.

A drug-resin complex is formed by reacting a resin with a drug using standard techniques. For example, a sodium salt of a resin may be reacted with a cationic drug. The amounts of drug and resin necessary to form an effective drug resin complex will vary greatly. Among the factors to be considered in determining the ratio of drug to resin are the particular drug, the resin used, the reaction conditions, and the final dosage form required. The resin preferably has a high loading capacity for the drug in question. A small loading capacity may make the resulting dosage form overly bulky or expensive to produce. Actual loading of the drug on the resin particles can range from about 1 to 90 percent by weight but preferably 5 to 30 percent by weight.

Preferably the chelating agent is added after the drug-resin complex is formed. The drug-resin complex may be dried before adding the chelating agent. EDTA or one of its salts is the preferred chelating agent. Neither resins nor drug-resin complexes are soluble in water, so reactions typically are carried out with the resin in suspension. The chelating agent may be added to the liquid in which the resin is suspended. EDTA preferably is added to an aqueous suspension of the drug-resin complex. The amount of EDTA should be an amount effective to significantly reduce degradation of the drug-resin complex.

The complex may also be treated by addition of a solvating or impregnating agent. Possible solvating agents include polyethylene glycol, glycerol, propylene glycol, mannitol, lactose, and methylcellulose. Polyethylene glycol (PEG) is preferred. The solvating agent typically is present in an amount of 5 to 35 parts by weight of the solvating agent to 100 parts by weight of the resin. EDTA most preferably is incorporated into the resin complex by converting the disodium salt to the tetrasodium salt in an aqueous solution of polyethylene glycol 3350. The EDTA/PEG solution is preferably about 1% EDTA by weight, but may range from about 0.1% to 50%. The amount of sodium hydroxide should be an amount effective to convert the EDTA present to the tetrasodium salt. The EDTA/PEG solution may be added to a dried drug-resin complex or to an undried complex. The content of EDTA in the drug-resin complex in the final dosage form may vary from about 0.001% to 10% by weight, but is preferably about 0.1 to 0.75% by weight for solid dosage forms and 0.005 to 0.2% by weight for suspensions. The mixture of drug-resin complex, chelating agent, and solvating agent may be dried to remove all but tightly bound water, or used without drying.

After the drug-resin complex is formed, it may be coated with a film forming polymer. Coating can slow the rate of dissolution and slow absorption of the drug in the gastrointestinal tract. An enteric coating may be used if it is desirable for the complex to dissolve only in the intestine and not in the stomach. Coatings can be of any film-forming material with diffusion barrier properties. Coatings chosen should not be toxic to humans and generally should not have any pharmacological effect alone. Conventional coating procedures such as those described in U.S. Pat. No. 4,221,778, whose entire contents are incorporated by reference herein, can be used to coat the particles, such as air suspension spray coating or fluid bed spray coating. Coatings generally are applied to the complex, but can be applied to the resin before complexing. Possible coating materials which can be used include ethylcellulose, methylcellulose, polyethylene glycol, mannitol, lactose and others in solvents such as ethanol, acetone and methylene chloride. EDTA may be added to an aqueous suspension of the coated drug-resin. Varying the amount of coating or combining coated and uncoated complexes in the same formulation can be used to adjust the dissolution profile as desired. The amount of coating used should be an amount effective to achieve the dissolution characteristics of the drug-resin complex desired for the particular dosage form. Coatings can be used to alter dissolution profiles for syrups, suspensions, suppositories, and capsules as well as for tablets.

The effectiveness of stabilization of a given drug-resin complex may be determined by assaying the complex for drug content or activity. The assay results for freshly prepared complex may be compared to results obtained after storage. The addition of the chelating agent to the drug-resin complex significantly improves the stability of the drug in the complex. A reduction in formation of degradation products is observed.

The drug-resin complexes of the present invention can be used in pharmaceutical compositions for oral, topical, rectal, vaginal, nasal, or ophthalmic administration. Possible dosage forms include tablets, capsules, powders, syrups, suspensions, lotions, creams, suppositories, nasal sprays, inhalers, and eye drops, with suspensions being the preferred mode of administration.

The present invention is further illustrated by the following Examples which are not intended to be limiting. It is to be understood by those skilled in the art that modifications and changes can be made thereto without departing from the spirit and scope of the invention.

EXAMPLE 1

Codeine sulfate (17.6 g) was dissolved in 700 mL of water. To the codeine sulfate solution, 656 g of a divinyl benzene sulfonic acid resin, sodium salt (AMBERLITE IRP 70, available from Rohm & Haas) was added and dispersed. The codeine sulfate solution and the resin were mixed for 2 hours, forming a drug-resin complex suspension in an aqueous vehicle. The resulting mixture was filtered using a screen centrifuge to remove the water.

Disodium edetate (3.6 g) and 0.8 g of sodium hydroxide were dissolved in 170 mL of water. Polyethylene glycol 3350 (213 g) was added to this solution and dissolved. The sodium hydroxide facilitates the dissolution of the disodium edetate in the aqueous polyethylene glycol, through formation of the tetrasodium salt of EDTA. The polyethylene glycol solution was added to the drug-resin complex suspension and mixed well. The resulting mixture was dried in a fluid bed dryer by passing warm air through the wet polyethylene glycol treated drug resin complex at a sufficient velocity to suspend the material being dried. The inlet air temperature was 25 to 50C. and the mixture was dried to a moisture content of 6 to 10% by weight. This drying resulted in an EDTA concentration of about 0.36% by weight.

EXAMPLE 2

A liquid suspension of dextromethorphan polistirex was prepared in an aqueous vehicle. The aqueous vehicle contained sucrose, high fructose corn syrup, microcrystalline cellulose, carboxymethylcellulose, xanthan gum, orange flavors, methyl and propylparaben, and propylene glycol.

Disodium edetate (0.05% by weight) was added to the suspension and dissolved.

Composition of the Liquid Suspension of Dextromethorphan Polistirex Before the Addition of Disodium Edetate

| | |
|---|---|
| Anhydrous Citric Acid | 2.0 g |
| Propylene Glycol | 60.0 g |
| Methylparaben | 1.5 g |
| Propylparaben | 0.3 g |
| High Fructose Corn Syrup | 300.0 g |
| Granulated Sugar | 120.0 g |
| Polysorbate 80 | 0.2 g |
| Microcrystalline Cellulose and Carboxymethylcellulose Sodium | 11.0 g |
| Xanthan Gum | 1.1 g |
| FD&C Yellow #6 | 0.023 g |
| Orange Flavor | 2.0 g |
| Purified Water q.s. ad | 1.0 L |

EXAMPLE 3

The dried, EDTA-containing drug resin of Example 1 was coated by spraying a coating solution of ethylcellulose, 50 cps, and vegetable oil dissolved in a solvent mixture of acetone and methylene chloride. The composition of coating solution (% by weight) was:

| | |
|---|---|
| Ethylcellulose, 50 cps | 3.4% |
| Vegetable Oil | 1.4% |
| Acetone | 6.3% |
| Methylene Chloride | 88.9% |

The coating solution was applied by spraying it onto a finely divided powder or granule of the PEG treated drug resin complex in an air suspension fluid bed processor (Wurster coater). The stability of this coated codeine-resin complex without added EDTA was compared to coated codeine-resin complex with EDTA added. Codeinone is a degradation product of codeine. The area percent of codeinone is therefore an indication of the degradation of the codeine. Codeine and codeinone were quantitated by extracting the resin with a 70% methanol in IN aqueous ammonium chloride solution and analyzing the extraction solution by HPLC. The percentage of codeinone was estimated by the proportionality of the areas of the codeine and codeinone peaks of the HPLC chromatograms as analyzed spectrophotometrically.

Without EDTA added, after 12 months at room temperature the data showed a decline of 20% in the amount of codeine present. At 37C., the decline was even more marked, 42% less codeine after 6 months. However, with EDTA added, there was a decline of only 4% in the amount of codeine after 25 months at room temperature. At 37C., only 11% less codeine was present after 6 months. The amount of codeinone present was also significantly less with EDTA added.

| Storage Conditions | Storage Time | % Codeine | % of Initial % Codeine | % Codeinone |
|---|---|---|---|---|
| Stability of Coated Codeine Drug-Resin No EDTA Added | | | | |
| Initial | none | 12.2 | | 0.7 |
| RT | 3 months | 11.2 | 92 | 1.4 |
| RT | 6 months | 10.5 | 86 | 2.6 |
| RT | 12 months | 9.8 | 80 | 6.0 |
| 37C | 3 months | 7.5 | 61 | 3.7 |
| 37C | 6 months | 7.1 | 58 | 5.0 |
| 37C | 12 months | 9.0 | 74 | 6.4 |
| Stability of Coated Codeine Drug-Resin EDTA Added | | | | |
| Initial | none | 11.8 | | <0.5 |
| RT | 3 months | 10.5 | 89 | <0.5 |
| RT | 6 months | 10.6 | 90 | <0.5 |
| RT | 9 months | 10.4 | 88 | <0.5 |
| RT | 12 months | 11.1 | 94 | <0.5 |
| RT | 25 months | 11.3 | 96 | <0.5 |
| 37C | 3 months | 10.8 | 92 | <0.5 |
| 37C | 6 months | 10.5 | 89 | <0.5 |

EXAMPLE 4

The stability of codeine in commercially available PENN-TUSS suspension was compared to an experimental PENN-TUSS suspension with 0.05% EDTA. Commercial PENN-TUSS suspension is an aqueous suspension containing codeine and chlorpheniramine drug-resin complexes. The experimental suspension contained the EDTA stabilized codeine polistirex from Example 3, plus additional disodium edetate. The total concentration of EDTA in the experimental suspension was 0.05% by weight. The data indicate less decline in codeine content in the suspension containing EDTA than in the suspension without EDTA. The amount of codeinone present was also generally less in the suspension containing EDTA.

The composition of the experimental suspension was as follows:

| Ingredients | Per Liter |
|---|---|
| Coated Codeine Polistirex | * |
| Chlorpheniramine Polistirex | ** |
| Cleargel Starch | 24.2 g |
| Xanthan Gum | 2.2 g |
| Granulated Sugar | 100.0 g |
| D & C Red #33 | 0.025 g |
| High Fructose Corn Syrup | 300.0 g |
| Propylene Glycol | 10.0 g |
| Methylparaben | 1.5 g |
| Propylparaben | 0.3 g |
| Cherry Cream Flavor | 2.86 g |
| Polysorbate 80 | 1.0 g |
| Disodium Edetate | 0.5 g |
| Purified Water q.s. ad | 1.0 Liter |

*Equivalent to 2.0 g codeine (base) (15.87 g/L Coated Codeine Polistirex containing 12.6% codeine (base))
**Equivalent to 0.80 g Chlorpheniramine Maleate (2.18 g/L Chlorpheniramine Polistirex containing 25.8% chlorpheniramine (base))

The commercial PENTUSS suspension had the same composition as the experimental suspension except that there was no EDTA in the codeine polistirex or in the suspension itself.

| Package Type | Storage Conditions | Storage Time | Codeine % of Theory | Area % Codeinone |
|---|---|---|---|---|
| Stability of Codeine in Commercial Penntuss Suspension No EDTA Added | | | | |
| Amber Pint | Initial | none | 99.8 | 2.4 |
| Amber Pint | RT | 1 month | 98.0 | 1.7 |
| Amber Pint | RT | 3 months | 99.4 | 0.9 |
| Amber Pint | RT | 6 months | 94.9 | 1.7 |
| Amber Pint | RT | 9 months | 99.4 | 1.6 |
| Amber Pint | RT | 12 months | 104.3 | 1.9 |
| Amber Pint | RT | 18 months | 101.1 | 1.7 |
| Amber Pint | RT | 24 months | 97.0 | 1.0 |
| Amber 3 oz. | Initial | none | 101.8 | 2.1 |
| Amber 3 oz. | RT | 1 month | 95.0 | 4.3 |
| Amber 3 oz. | RT | 3 months | 92.0 | Trace |
| Amber 3 oz. | RT | 6 months | 95.2 | 3.5 |
| Amber 3 oz. | RT | 9 months | 94.3 | 2.9 |
| Amber 3 oz. | RT | 12 months | 93.2 | 4.0 |
| Amber 3 oz. | RT | 18 months | 88.1 | 5.7 |
| Amber 3 oz. | RT | 24 months | 84.9 | 2.4 |

Note: ND means not detected.

| Package Type | Storage Conditions | Storage Time | Codeine % of Desired | Area % Codeinone |
|---|---|---|---|---|
| Stability of Codeine in Experimental Penntuss 0.05% EDTA Added | | | | |
| Amber Pint | Initial | none | 100.6 | 0.6 |
| Amber Pint | RT | 3 months | 100.0 | 0.6 |
| Amber Pint | RT | 6 months | 100.8 | 1.3 |
| Amber Pint | RT | 12 months | 101.4 | <1.0 |
| Amber Pint | Initial | none | 98.7 | 0.6 |
| Amber Pint | RT | 3 months | 98.7 | 0.8 |
| Amber Pint | RT | 6 months | 98.4 | 1.3 |
| Amber Pint | RT | 12 months | 99.7 | <1.0 |
| Amber 3 oz. | Initial | none | 96.4 | 0.7 |
| Amber 3 oz. | RT | 3 months | 97.8 | 0.9 |
| Amber 3 oz. | RT | 6 months | 98.8 | 1.6 |
| Amber 3 oz. | RT | 12 months | 95.5 | 1.2 |

Note: The package types are types of glass bottles.

EXAMPLE 5

The stability of dextromethorphan polystirex drug-resin suspensions with and without 0.05% disodium edetate by weight was compared. The desired amount was 30 mg dextromethorphan per 5 mL of suspension. The data indicated that without EDTA, the dextromethorphan content declined 10% in 18 months. With EDTA present, there was no decline in dextromethorphan content over 18 months. The dextromethorphan polistirex drug-resin suspensions tested in the table below were made by preparing coated dextromethorphan polistirex and suspending the coated dextromethorphan polistirex in a sufficient quantity of water so that there were 30 mg dextromethorphan per 5 mL of suspension.

Uncoated dextromethorphan polistirex was prepared by reacting 381.7 g of dextromethorphan hydrochloride with 673 g of AMBERLITE IRP-70, sodium cycle resin, in 4.2 L of purified water for 4 hours and subsequently filtering the reacted dextromethorphan polistirex using a basket centrifuge. The filtered resin was then dried in a fluid bed dryer.

Coated dextromethorphan polistirex was prepared by reacting 381.7 g of dextromethorphan hydrochloride with 673 g of AMBERLITE IRP-70, sodium cycle resin, in 4.2 L of purified water for 4 hours and subsequently filtering the reacted dextromethorphan polistirex using a basket centrifuge. The dextromethorphan polistirex was then mixed with a solution of 227 g of polyethylene glycol 3350 dissolved in 360 ml of purified water. This mixture was then dried in a fluid bed dryer. The dried material was then milled through a Comil grinder and coated with the same ethylcellulose coating solution as described in Example 3.

The dextromethorphan drug-resin suspensions tested in the table below contained a mixture of coated and uncoated dextromethorphan drug-resin. The ratio of coated to uncoated drug-resin does not affect the rate of degradation of the drug. The ratio of coated to uncoated drug-resin in the examples below was approximately 2:1 coated/uncoated. However, the range of coated/uncoated drug-resin can range from 9:1 to 1:9.

Dextromethorphan ketone, (−)-3-methyl-10-oxy-methylmorphinan, is a degradation product of dextromethorphan. Dextromethorphan and dextromethorphan ketone were quantitated by separating the resin from the suspension by filtration on a fritted glass funnel and then extracting the resin with a 70% methanol in 1N aqueous ammonium chloride solution and analyzing the extraction solution by HPLC. The percentage of dextromethorphan ketone was estimated by the proportionality of the areas of the dextromethorphan and dextromethorphan ketone peaks of the HPLC chromatograms as analyzed spectrophotometrically.

Stability of Dextromethorphan Drug-Resin Suspensions

| Storage Conditions | Storage Time | Dextromethorphan % of Desired No EDTA Added | Dextromethorphan % of Desired 0.05% EDTA Added |
|---|---|---|---|
|  | Initial | 102 | 104 |
| RT | 3 months | 93 | 102 |
| RT | 6 months | 96 | 105 |
| RT | 9 months | 89 | 103 |
| RT | 12 months | 94 | 101 |
| RT | 18 months | 92 | 104 |

The above description is provided for the purpose of describing embodiments of the invention and is not intended to limit the scope of the invention in any way. It will be apparent to those skilled in the art that various modifications and variations can be made in the drug-resin complexes stabilized by chelating agents, their methods of manufacture, and their uses without departing from the spirit or scope of the invention. Thus, it is intended that the present invention cover the modifications and variations of this invention provided they come within the scope of the appended claims and their equivalents.

What is claimed is:

1. A pharmaceutical composition comprising a drug-resin complex and a chelating agent,
   wherein the composition is in the form of a solid or a gel,
   wherein the chelating agent is present in an amount effective to reduce the amount of degradation of the drug in the drug resin complex by more than 20 percent over twelve months of storage at room temperature relative to an otherwise identical pharmaceutical composition without the chelating agent;
   wherein the changing agent is selected from EDTA or a salt of EDTA; and
   wherein the drug in the drug-resin complex is selected from dextromethorphan, codeine, morphine, hydrcodone, pseudoephedrine, or phenylpropanolamine.

2. A pharmaceutical composition according to claim 1, wherein the composition is in the form of a solid.

3. A pharmaceutical composition according to claim 1, wherein the resin in the drug-resin complex is a cationic exchange resin.

4. A pharmaceutical composition according to claim 3, wherein the resin is a divinylbenzene sulfonic acid cationic exchange resin.

5. A pharmaceutical composition according to claim 1, wherein the chelating agent is not covalently bound to the drug resin complex.

6. A pharmaceutical composition according to claim 1, wherein the chelating agent is covalently bound to the drug resin complex.

7. A pharmaceutical composition according to claim 1, wherein the chelating agent is present in a concentration of from 0.001 to 10 percent by weight.

8. A pharmaceutical composition according to claim 1, wherein the chelating agent is present in a concentration of from 0.1 to 5 percent by weight.

9. A pharmaceutical composition according to claim 1, wherein the drug-resin complex comprises a diffusion barrier coating.

10. A pharmaceutical composition according to claim 9, wherein the diffusion barrier coating is an enteric coating.

11. A pharmaceutical composition according to claim 1, wherein the drug-resin complex comprises a solvating agent.

12. A pharmaceutical composition according to claim 11, wherein the solvating agent is polyethylene glycol.

13. A pharmaceutical composition according to claim 1, wherein the drug-resin complex comprises a solvating agent and a diffusion barrier coating.

14. A pharmaceutical composition according to claim 1, wherein the pharmaceutical composition is suitable for oral, topical, rectal, vaginal, nasal, or ophthalmic administration.

15. A pharmaceutical composition according to claim 1, wherein the pharmaceutical composition is in the form of a tablet, a capsule, a powder, a lotion, a cream, or a suppository.

16. A pharmaceutical composition according to claim 14, wherein the pharmaceutical composition is suitable for oral administration.

17. A method of making a pharmaceutical composition comprising:
   (a) combining a drug and an ion exchange resin in a liquid to form a drug-resin complex;
   (b) adding a chelating agent; and
   (c) drying the result of step (b) to form a solid or gel pharmaceutical composition,
   wherein the chelating agent is present in an amount effective to reduce the amount of degradation of the drug in the drug resin complex by more than 20 percent over twelve months of storage at room temperature relative to an otherwise identical pharmaceutical composition without the chelating agent;
   wherein the chelating agent is selected from EDTA or a salt of EDTA; and
   wherein the drug in the drug-resin complex is selected from dextromethorphan, codeine, morphine, hydrcodone, pseudoephedrine, or phenylpropanolamine.

18. A method of making a pharmaceutical composition comprising:
   (a) combining a drug and an ion exchange resin in a liquid to form a drug-resin complex;
   (b) adding a chelating agent;
   (c) drying the result of step (b) to form a solid; and
   (d) suspending the result of step (c) in an appropriate liquid to form a liquid pharmaceutical composition,
   wherein the chelating agent is present in an amount effective to reduce the amount of degradation of the drug in the drug resin complex by more than 20 percent over twelve months of storage at room temperature relative to an otherwise identical pharmaceutical composition without the chelating agents;

wherein the chelation agent is selected from EDTA or a salt of EDTA; and wherein the drug in the drug-resin complex is selected from dextromethorphan, codeine, morphine, hydrcodone, pseudoephedrine, or phenylpropanolamine.

19. A method of making a pharmaceutical composition comprising:

(a) combining a drug and an ion exchange resin in a first liquid to form a drug-resin complex;

(b) drying the result of step (a) to form a solid;

(c) suspending the result of step (b) in an appropriate second liquid, which may be the same or different than the first liquid; and (d) adding a chelating agent, to form a liquid pharmaceutical composition, wherein the chelating agent is present in an amount effective to reduce the amount of degradation of the drug in the drug resin complex by more than 20 percent over twelve months of storage at room temperature relative to an otherwise identical pharmaceutical composition without the chelating agent, wherein the chelating agent is selected from EDTA or a salt of EDTA; and wherein the drug in the drug-resin complex is selected from dextromethorphan, codeine, morphine, hydrcodone, pseudoephedrine or phenylpropanolamine.

20. A pharmaceutical composition prepared by the process of:

(a) combining a drug and an ion exchange resin in a liquid to form a drug-resin complex;

(b) adding a chelating agent; and (c) drying the result of step (b) to form a solid or gel pharmaceutical composition, wherein the chelating agent is present in an amount effective to reduce the amount of degradation of the drug in the drug resin complex by more than 20 percent over twelve months of storage at room temperature relative to an otherwise identical pharmaceutical composition without the chelating agent;

wherein the chelating agent is selected from EDTA or a salt of EDTA; and wherein the drug in the drug-resin complex is selected from dextromethorphan, codeine, morphine, hydrcodone, pseudephedrine, or phenylpropanolamine.

21. A pharmaceutical composition prepared by the process of:

(a) combining a drug and an ion exchange resin in a liquid to form a drug-resin complex;

(b) adding a chelating agent;

(c) drying the result of step (b) to form a solid; and (d) suspending the result of step (c) in an appropriate liquid to form a liquid pharmaceutical composition, wherein the chelating agent is present in an amount effective to reduce the amount of degradation of the drug in the drug resin complex by more than 20 percent over twelve months of storage at room temperature relative to an otherwise identical pharmaceutical composition without the chelating agent;

wherein the chelating element is selected from EDTA or a salt of EDTA; and wherein the drug in the drug-resin complex is selected from dextromethorphan, codeine, morphine, hydrcodone, pseudoephedrine, or phenylpropanolamine.

22. A pharmaceutical composition prepared by the process of:

(a) combining a drug and an ion exchange resin in a first liquid to form a drug-resin complex;

(b) drying the result of step (a) to form a solid;

(c) suspending the result of step (b) in an appropriate second liquid, which may be the same or different than the first liquid; and (d) adding a chelating agent, to form a liquid pharmaceutical composition, wherein the chelating agent is present in an amount effective to reduce the amount of degradation of the drug in the drug resin complex by more than 20 percent over twelve months of storage at room temperature relative to an otherwise identical pharmaceutical composition without the chelating agent;

wherein the chelating agent is selected from EDTA or a salt of EDTA; and wherein the drug in the drug-resin complex is selected from dextromethorphan, codeine, morphine, hydrcodone, pseudoephedrine, or phenylpropanolamine.

23. A method for improving the stability of a pharmaceutical composition that contains a drug-resin complex comprising adding a chelating agent in an amount effective to reduce the rate of degradation of the drug in the drug-resin complex by more than 20 percent over twelve months of storage at room temperature relative to an otherwise identical pharmaceutical composition without the chelating agent;

wherein the chelating agent is selected from EDTA or a salt of EDTA; and wherein the drug in the drug-resin complex is selected from dextromethorphan, codeine, morphine, hydrocodone, pseudoephedrine, or phenylpropanolamine.

24. A method according to claim 23, wherein the composition is a solid.

25. A method according to claim 23, wherein the composition is a gel.

26. A method according to claim 23, wherein the composition is a suspension.

27. A method for administering a drug to a patient in need thereof, comprising:

(a) providing a pharmaceutical composition that contains a drug-resin complex that contains the drug;

(b) adding a chelating agent;

(c) storing the combination of step (b); and (d) subsequently administering the combination of step (b) to the patient, wherein the chelating agent is present in an amount effective to reduce the amount of degradation of the drug in the drug resin complex by more than 20 percent over twelve months of storage at room temperature relative to an otherwise identical pharmaceutical composition without the chelating agent;

wherein the chelating agent is selected from EDTA or a salt of EDTA; and wherein the drug in the drug-resin complex is selected from dextromethorphan, codeine, morphine, hydrocodone, pseudoephedrine, or phenylpropanolamine.

28. A pharmaceutical composition according to claim 1, wherein the drug in the drug-resin complex is dextromethorphan.

29. A pharmaceutical composition according to claim 1, wherein the drug in the drug-resin complex is codeine.

30. A method according to claim 17, wherein the drug in the drug-resin complex is dextromethorphan.

31. A method according to claim 17, wherein the drug in the drug-resin complex is codeine.

32. A method according to claim 17, wherein the drug in the drug-resin complex is dextromethorphan.

33. A method according to claim 18, wherein the drug in the drug-resin complex is codeine.

34. A method according to claim 19, wherein the drug in the drug-resin complex is dextromethorphan.

35. A method according to claim 19, wherein the drug in the drug-resin complex is codeine.

36. A method according to claim 23, wherein the drug in the drug-resin complex is dextromethorphan.

37. A method according to claim 23, wherein the drug in the drug-resin complex is codeine.

* * * * *

UNITED STATES PATENT AND TRADEMARK OFFICE
CERTIFICATE OF CORRECTION

PATENT NO. : 5,980,882
DATED : November 9, 1999
INVENTOR(S) : Martin L. Eichman

It is certified that error appears in the above-identified patent and that said Letters Patent is hereby corrected as shown below:

Column 6, line 63, replace "Zwitterinonic" with --Zwitterionic--.
Column 10, line 67, replace "sedatuves" with --sedatives--.
Claim 1, line 14, replace "hydrcodone" with --hydrocodone--.
Claim 17, line 18, replace "hydrcodone" with --hydrocodone--.
Claim 18, column 19, line 5, replace "chelation" with --chelating--; line 8, replace "hydrcodone" with --hydrocodone--.
Claim 19, line 21, replace "hydrcodone" with --hydrocodone--.
Claim 20, line 18, replace "hydrcodone" with --hydrocodone--.
Claim 21, line 15, replace "element" with --agent--; column 20, line 3, replace "hydrcodone" with --hydrocodone--.
Claim 22, line 21, replace "hydrcodone" with --hydrocodone--.
Claim 32, line 1, replace "17" with --18--.
Column 7, line 33, replace "antifingals" with --antifungals--.
Column 8, line 13, replace "befimolol" with --befunolol--.
Column 8, line 48, replace "metharnphetamine" with --methamphetamine--.
Column 9, line 12, replace "arnikacin" with --amikacin--.
Column 9, line 16, replace "andinocillin" with --amdinocillin--.
Column 9, line 42, replace "butenafme" with --butenafine--.
Column 10, line 52, replace "ahnitrine" with --almitrine--.
Column 11, line 26, replace "cmepazide" with --cinepazide--.
Column 11, line 33, replace "arstiinol" with --arsthinol--.
Column 14, line 53, replace "IN" with --1N--.

Signed and Sealed this

Thirtieth Day of January, 2001

Attest:

Attesting Officer

Q. TODD DICKINSON
Director of Patents and Trademarks